(12) United States Patent
Nemanic et al.

(10) Patent No.: US 11,090,130 B2
(45) Date of Patent: Aug. 17, 2021

(54) FIDUCIAL MARKER FOR COMPUTED TOMOGRAPHY AND MAGNETIC RESONANCE IMAGING

(71) Applicant: Oregon State University, Corvallis, OR (US)

(72) Inventors: Sarah Nemanic, Corvallis, OR (US); Jesse L. Terry, Corvallis, OR (US); Milan Milovancev, Corvallis, OR (US); Josiah Moses, Corvallis, OR (US); Rebecca A. Francis, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 696 days.

(21) Appl. No.: 15/289,015

(22) Filed: Oct. 7, 2016

(65) Prior Publication Data

US 2017/0100202 A1    Apr. 13, 2017

Related U.S. Application Data

(60) Provisional application No. 62/239,417, filed on Oct. 9, 2015.

(51) Int. Cl.
| | | |
|---|---|---|
| *A61B 5/00* | (2006.01) | |
| *A61B 5/055* | (2006.01) | |
| *A61B 90/00* | (2016.01) | |
| *A61B 6/03* | (2006.01) | |
| *A61B 6/00* | (2006.01) | |

(52) U.S. Cl.
CPC ............... *A61B 90/39* (2016.02); *A61B 6/032* (2013.01); *A61B 6/4417* (2013.01); *A61B 6/5258* (2013.01); *A61B 6/583* (2013.01); *A61B 5/0035* (2013.01); *A61B 5/055* (2013.01); *A61B 2090/3933* (2016.02); *A61B 2090/3954* (2016.02); *A61B 2090/3966* (2016.02); *A61B 2090/3995* (2016.02)

(58) Field of Classification Search
CPC ....... A61B 90/39; A61B 6/583; A61B 6/5258; A61B 6/4417; A61B 6/032; A61B 2090/3933; A61B 2090/3995; A61B 2090/3954; A61B 5/0035; A61B 5/055
See application file for complete search history.

(56) References Cited

U.S. PATENT DOCUMENTS

| | | | | |
|---|---|---|---|---|
| 6,333,971 B2 * | 12/2001 | McCrory | ........... | A61K 49/0409 378/162 |
| 8,798,716 B1 * | 8/2014 | DeSena | .................. | A61B 90/39 600/414 |
| 2008/0234532 A1 * | 9/2008 | De Langen | ............ | A61B 90/39 600/8 |
| 2014/0065076 A1 * | 3/2014 | Hollander | .......... | A61K 49/0404 424/9.452 |
| 2015/0011861 A1 * | 1/2015 | Rahmer | ............... | A61B 5/0071 600/409 |

OTHER PUBLICATIONS

Terry, Jesse L., Milan Milovancev, and Sarah Nemanic. "In Vitro Evaluation of a Novel Fiducial Marker for Computed Tomography and Magnetic Resonance Imaging of Soft Tissues in Small Animals." American journal of veterinary research 75.11 (2014): 974-981. (Year: 2014).*

* cited by examiner

*Primary Examiner* — Robert A Wax
*Assistant Examiner* — Nabila G Ebrahim
(74) *Attorney, Agent, or Firm* — Schwabe, Williamson & Wyatt, P.C.

(57) ABSTRACT

Disclosed herein are fiducial markers that include a sealed casing member containing a mixture of iodine and water that includes about 1-300 mg/ml iodine. The fiducial markers may be distinguishable on at least two imaging modalities, such as CT and MRI. The casing member may include a plastic or elastomeric material, such as polyvinyl chloride (PVC) polypropylene, latex, nylon, dynaflex, and may take the form of a length of IV tubing sealed at each of two ends. The length of IV tubing may be crimped to form a desired shape, such as a triangle. Also disclosed are methods of making fiducial markers that are distinguishable on at least two imaging modalities, such as CT and MRI.

16 Claims, 10 Drawing Sheets

Figure 6A
Figure 6B
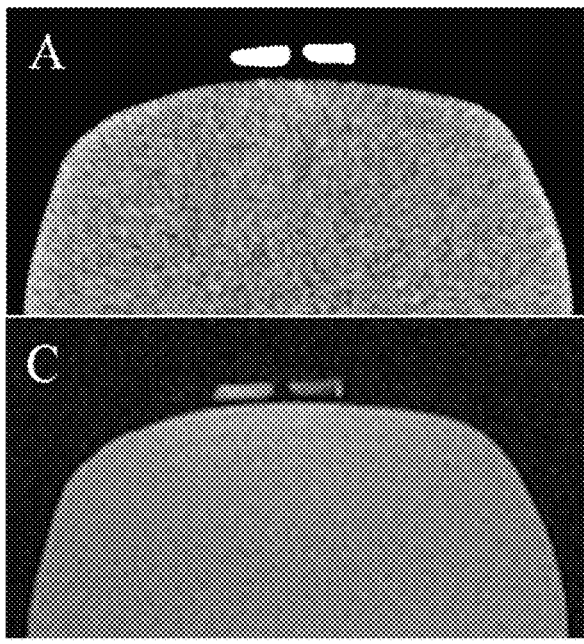
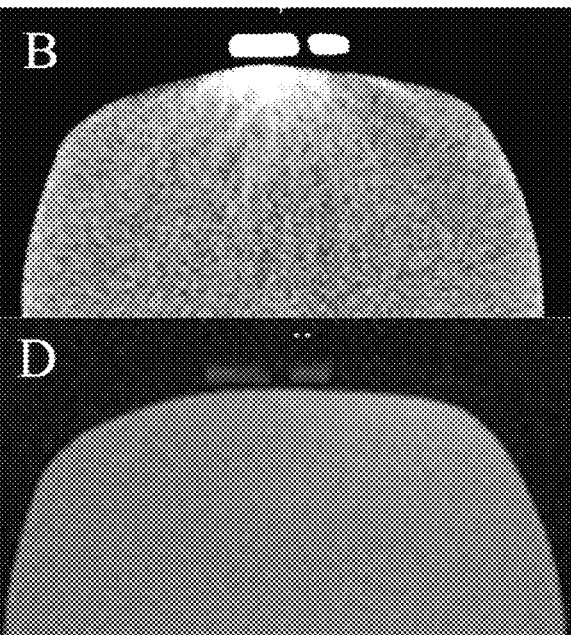
Figure 6C
Figure 6D

FIDUCIAL MARKER FOR COMPUTED TOMOGRAPHY AND MAGNETIC RESONANCE IMAGING

CROSS-REFERENCE TO RELATED APPLICATION

This application claims the benefit of the filing date of U.S. Provisional Patent Application No. 62/239,417, filed Oct. 9, 2015, entitled "FIDUCIAL MARKER FOR COMPUTED TOMOGRAPHY AND MAGNETIC RESONANCE IMAGING," the disclosure of which is incorporated herein in its entirety.

TECHNICAL FIELD

Embodiments relate to markers for imaging applications, such as computed tomography (CT) and magnetic resonance imaging (MRI).

BACKGROUND

A fiducial marker is a material fixed on, or within, the body near a target of interest that is visible during imaging procedures. A fiducial marker acts as a common reference point, linking the location of the disease on CT or MRI images to the location of the disease within the patient. Fiducial markers typically are used for surgical planning and/or radiotherapy. For instance, in veterinary medicine, a needle may be placed into the spinous process of a vertebra to guide the surgeon to the correct disc space during decompressive spinal surgery. In other applications, bony landmarks or previously placed vascular clips may be used as fiducial markers. In human medicine, fiducial markers may allow synchronization of the radiation beam between treatments to moving organs, such as the heart or lungs, thereby decreasing target margin and dose to surrounding tissues. Similarly, the use of fiducial markers in image-guided radiation therapy for partial breast irradiation allows a decrease in planning target volume margins, and fiducial marker registration (superimposition of previous images onto intraoperative surgical anatomic structures) may be used during the preoperative planning process in patients that undergo perforator flap reconstructive procedures. Likewise, fiducial-based localization of the vertebral column prior to neurosurgery is a standard protocol. However, a fiducial marker that is easily visualized via CT is not necessarily visible on MRI, and vice versa.

SUMMARY

Disclosed in various embodiments are fiducial markers that include a sealed casing member containing a mixture of iodine and water that includes about 1-300 mg/ml iodine, and that are distinguishable on at least two imaging modalities, such as CT and/or MRI. In some embodiments, the mixture of iodine and water comprises about 1-150 mg/ml iodine, about 1-60 mg/ml iodine or about 30 mg/ml iodine. In various embodiments, the casing member may include a plastic or elastomeric material, such as polyvinyl chloride (PVC) polypropylene, latex, nylon, or dynaflex, and in some embodiments, the plastic or elastomeric material may include a length of IV tubing sealed at each of two ends. In particular embodiments, the IV tubing is crimped to form a desired shape, such as a triangle. In some embodiments, one or more sides or corners of the fiducial marker may include a feature that functions as a positional indicator to assist in identifying the orientation of the marker in one or more imaging modalities.

Other embodiments are methods of making a fiducial marker, such methods including filling a casing member with a mixture of iodine and water that includes about 1-300 mg/ml iodine, and optionally sealing the casing member and/or forming the sealed casing member into a desired shape. In some embodiments, the mixture includes about 1-150 mg/ml iodine, or about 1-600 mg/ml iodine. In various embodiments, the casing member includes a plastic or elastomeric material, such as polyvinyl chloride (PVC) polypropylene, latex, nylon, or dynaflex, whereas in other embodiments, the plastic or elastomeric material may be a length of IV tubing sealed at each of two ends. In some embodiments, one or more sides or angles of the fiducial marker may be provided with a feature that functions as a positional indicator to assist in identifying the orientation of the marker in one or more imaging modalities.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 6A-6D illustrate four representative computed tomography (FIGS. 6A and 6B) and magnetic resonance imaging (FIGS. 6C and 6D) of markers containing 10% (FIGS. 6A and 6C) and 70% (FIGS. 6B and 6D) contrast medium, in accordance with various embodiments.

DETAILED DESCRIPTION OF DISCLOSED EMBODIMENTS

Figure 1A:
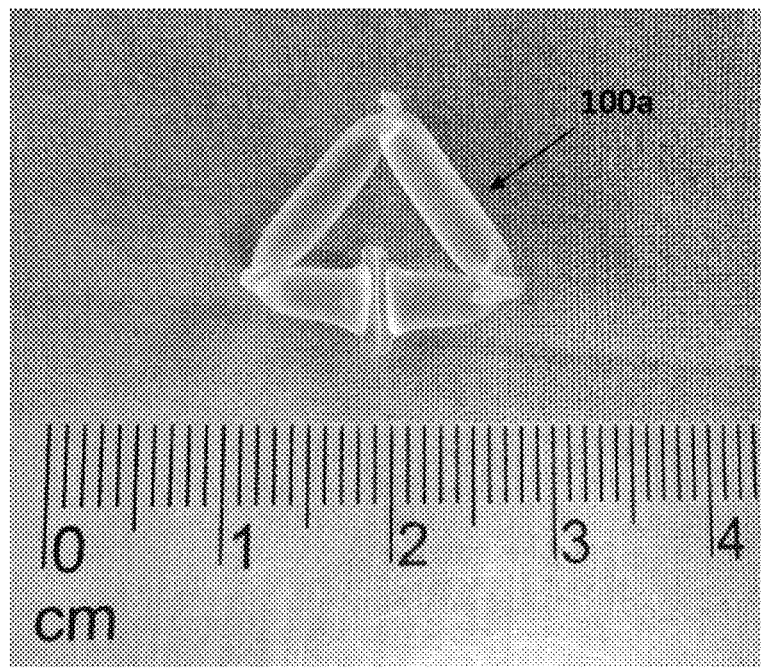
FIGS. 1A-1J include a digital image of one example of a fiducial marker with a side crimp positional indicator (FIG. 1A), an illustration of a triangular fiducial marker with a positional indicator on one side (FIG. 1B), a schematic diagram of a triangular fiducial marker with a positional marker on one side (FIG. 1C), a schematic diagram of a triangular fiducial marker with a positional indicator near one corner (FIG. 1D), a schematic diagram of a triangular fiducial marker with crimped corners (FIG. 1E), a partial cutaway view of a triangular fiducial marker showing a filled lumen (FIG. 1F), a schematic diagram of a rectangular fiducial marker (FIG. 1G), a schematic diagram of a circular fiducial marker (FIG. 1H), a schematic diagram of an arrow-shaped fiducial marker (FIG. 1I), and a schematic diagram of a rhomboid fiducial marker (FIG. 1J), all in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide fiducial markers that are simple to construct, inexpensive, and easily distinguishable on multiple advanced imaging modalities from the surrounding tissues to which they are applied. In various embodiments, the fiducial markers may be fluid-filled plastic or elastomeric members that may include a mixture of water and 1-300 mg/mg iodine. In some embodiments, the iodine may be supplied in the form of an iodinated contrast medium, for example a contrast medium that includes 3 caged iodine atoms per molecule as a monomer, such as iopamidol, iopromide, or iohexol. In various embodiments, the fiducial marker may be filled with a solution that consists only of the iodinated contrast medium and water (or another aqueous solution, such as a buffer). In various embodiments the mixture of water and iodine may include about 1-300 mg/ml iodine in water, about 1-150 mg/ml iodine in water, about 1-60 mg/ml iodine in water, or about 30 mg/ml iodine in water. In various embodiments, the mixture may be sealed inside a plastic or elastomeric member that has been formed into a desired shape, such as a triangle, square, circle, oval, or any desired shape. In various embodiments, the shape of the marker is formed to outline an area of interest on a patient. In various embodiments, the plastic or elastomeric material may include polyvinyl chloride (PVC) with or without diethylhexylphthalate (DEHP), polypropylene, latex, nylon, dynaflex, or any other polymeric material suitable for medical use that does not cause artifacts in the selected imaging modalities. In specific embodiments, the fiducial markers may be formed from medical tubing, such as IV tubing, filled with a solution of 1-300 mg/ml iodine in water, heat sealed, and crimped into a desired shape, such as a triangle. In various embodiments, such fiducial markers may provide sufficient attenuation/intensity to be seen on both CT and MRI, without excessive beam hardening artifact on CT.

In various embodiments, to assign the fiducial marker a polarity or directionality, an additional feature may be included in or near one or more sides or corners of the fiducial marker. In various embodiments, this positional indicator may be placed in a chosen relationship to the patient so that it may be visualized on one or more imaging modalities. In general, any feature may be used for a positional indicator, so long as it is visible on a desired imaging modality and does not create undesirable imaging artifacts. Specific, non-limiting examples of suitable positional indicators include a crimp in one or more sides or corners, a physical compression, constriction, or extension, or an augmentation, such as a fold, ridge, crease, wrinkle, bead, or a clip, such as a metal clip. In various embodiments, such a clip (or other augmentation) may be attached to the body of imaging device at any position that helps define marker orientation.

Another example of a suitable augmentation for use as a positional indicator is a suture ligand, ligature, or other strand, which may be tied around the body of the fiducial marker to provide a slight bend that may be appreciated on imaging and help identify position/orientation of the fiducial marker. In still other embodiments, the length of the sides of the triangle of the fiducial marker may be varied in order to function as a positional indicator. For instance, in some embodiments, the triangle formed by the fiducial marker may be asymmetrical.

In other embodiments, the fiducial marker may be formed in a different shape, such as a circle, rectangle, rhombus, star, paralellogram, hexagram, pentagram, square, star, or arrow. In still other embodiments, the fiducial marker may be foremed in the shape of a letter, number, word, or other indicia. In some embodiments, the fiducial marker may have sides that form a closed shape having a central "imaging area" portion that may be positioned about the tissue structure to be imaged. For instance, the open center portion of the triangle, circle, or square (etc.) may be used to indicate a tissue structure of interest.

The ability to use fiducial markers with multiple imaging modalities is of particular interest, as it is well known that different imaging modalities vary in their ability to show different tissue types. Thus, diagnostic and therapeutic protocols utilizing both MRI and CT are frequently encountered, and software is readily available to "fuse" images from each modality. Additional advantages of the fiducial markers disclosed herein are in that they do not create imaging artifacts and that they do not disturb the spatial relationships of the surrounding tissues.

In various embodiments, the fiducial markers disclosed herein may include iopamidol, an iodinated, nonionic, low-osmolarity contrast agent that is primarily used in angiography and excretory urography, or another iodinated contrast medium such as iopromide or iohexol. In various embodiments, iodinated contrast agents such as iopamidol may present certain challenges when they are used in fiducial markers. Specifically, the production of beam hardening and streaking artifacts is well documented with iodinated contrast agents. Beam hardening occurs when low energy photons are preferentially absorbed when a polychromatic x-ray passes through the material. This produces regions of streaking around the material in question, thereby obscuring the imaging of the tissues adjacent to it, which is clearly an undesirable trait in a fiducial marker.

As MRI does not rely on x-ray attenuation, beam hardening artifacts have not been reported with iodinated contrast agents. A variety of both positive and negative contrast materials have been evaluated for use with MRI. For example, vitamin E has been used to delineate laterality on MRI, but has been shown to be an inaccurate marker for surgical planning. Conveniently, the presence of water within a marker can act as a contrast agent itself and allow adequate MRI visualization on many commonly used pulse sequences, such as short tau inversion recovery (STIR) or T2-weighted images. Thus, as disclosed herein, a suitable fiducial marker may include an appropriate ratio of iodinated contrast medium to water, such that it is easily seen on both CT and commonly used MR pulse sequences, while minimizing beam hardening artifact on CT. In various embodiments, the disclosed fiducial markers may be formed in a shape that may be sutured to the skin, and that may be used for both surgical planning and/or radiotherapy.

Prior to the present disclosure, no cost effective, consistent, and reliable fiducial markers were available that may be used for both CT and MRI. The design and testing of such markers is described in detail below in various working Examples, which are intended to be construed as specific examples of the disclosed devices and methods, and are not to be taken as limiting.

EXAMPLES

Example 1: Fiducial Markers

Fiducial markers were made from 15 drop/ml intravenous drip tubing sets (Interlink® System Solution Set, Baxter, Deerfield, Ill.) This choice was made based on their low cost and widespread availability. Four to five centimeter sections were cut and used to make the markers. Serial dilutions of a commercially available 300 mg iodine/ml iopamidol solution and water were made (Isovue-300, iopamidol 61%, Bracco Diagnostics Inc, Princeton, N.J.) Iopamidol Injection 61% provides 612 mg iopamidol with 1 mg tromethamine and 0.39 mg edetate calcium disodium. The solution contains approximately 0.043 mg (0.002 mEq) sodium and 300 mg organically bound iodine per mL. Dilutions increased in 10% increments ranging from 0 to 100% of the iopamidol solution. These solutions were infused into the IV tubing sections, which were then sealed together using a commercially available IV tubing sealer (Terumo® Medical Corporation, Tokyo, Japan.) The markers were then sealed in two additional, equally spaced corners, creating a roughly equal sided triangle with 1.5 cm sides. FIG. 1A illustrates a digital image of one example of a fiducial marker, in accordance with various embodiments. Care was taken to prevent infusion of air into the tubing. To assign the markers a polarity, an additional crimp was created in one of the three sides using the IV sealer. In a clinical setting, this crimp may be used as a marker of directionality (e.g., the crimp may serve as a positional indicator and the crimped side may be placed in a chosen relationship to the patient).

Although the embodiment used in this Example was a triangular fiducial marker with a crimp in the center portion of one side, one of skill in the art will appreciate that the size and shape of the fiducial marker, and the position and type of positional indicator, may be varied to suit the particular application. For example, FIG. 1A is a digital image of a fiducial marker 100*a* with a side crimp positional indicator as described above, whereas FIGS. 1B-1J include an illustration of a triangular fiducial marker with a positional indicator on one side (FIG. 1B), a schematic diagram of a triangular fiducial marker with a positional marker on one side (FIG. 1C), a schematic diagram of a triangular fiducial marker with a positional indicator near one corner (FIG. 1D), a schematic diagram of a triangular fiducial marker with crimped corners (FIG. 1E), a partial cutaway view of a triangular fiducial marker showing a filled lumen (FIG. 1F), a schematic diagram of a rectangular fiducial marker (FIG. 1G), a schematic diagram of a circular fiducial marker (FIG. 1H), a schematic diagram of an arrow-shaped fiducial marker (FIG. 1I), and a schematic diagram of a rhomboid fiducial marker (FIG. 1J), all in accordance with various embodiments.

Figure 1B:
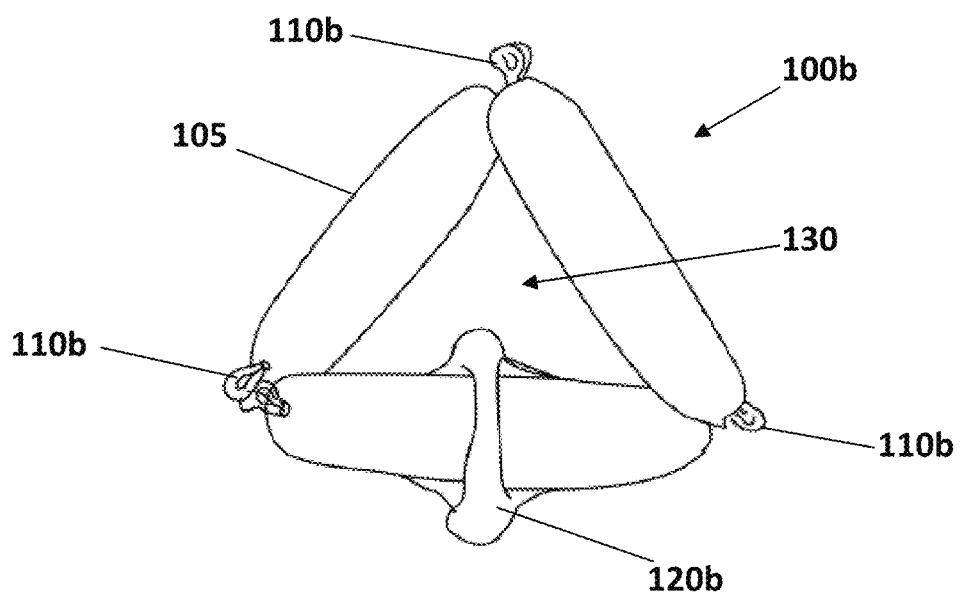

Referring now to FIG. 1B, the fiducial marker 100*b* may include a sealed casing member 105 having a triangular shape formed by three crimped or folded corners 110*b*, a central imaging area 130 for indicating an area of interest, and a positional indicator 120 centered on one side of the fiducial marker 100*b*. Although a triangular shape is shown, any desirable shape may be used. By way of example, the sealed casing member 105 may be formed in the shape of a square, rectangle, rhombus, triangle, circle, hexagon, pentagon, parallelogram, arrow, letter, number, word, or any other desired shape. The size of the sealed casing member 105 and length of its sides may be any size or length that provides for a desired imaging area 130. For example, in various embodiments, the length of a side may be from 0.1 to 100, 0.5 to 75, 1.0 to 50, 1.0 to 10, 1.0 to 5, or 1.0 to 2.0 cm in length. In various embodiments, the imaging area 130 may be determined by the shape of the sealed casing member 105 and the length of its sides, and may be an area suitable for MRI or CT imaging purposes.

Figure 1C:
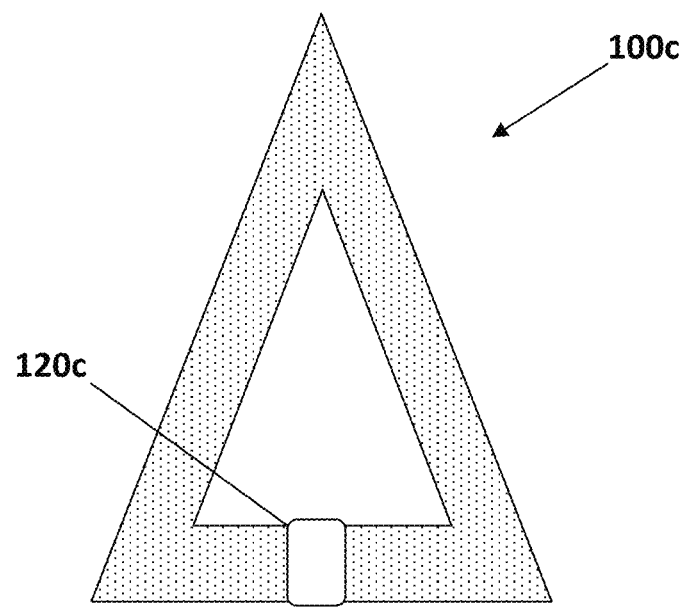
Figure 1D:
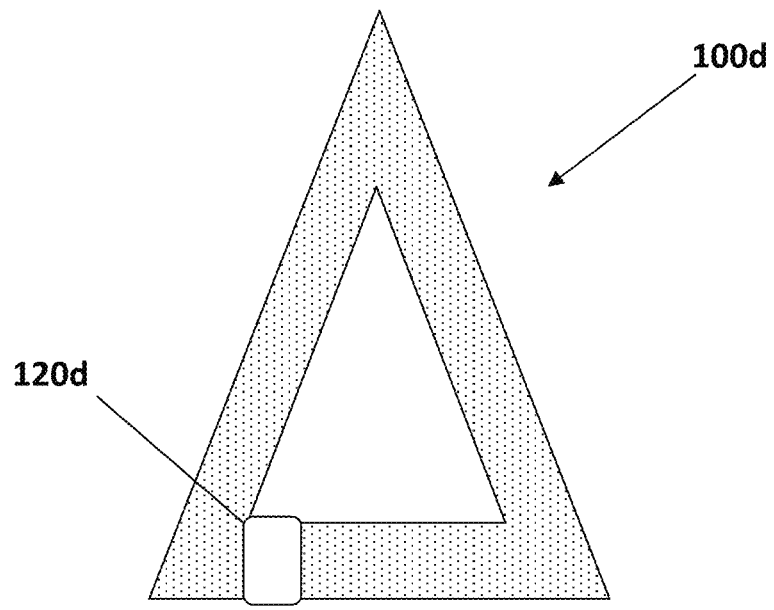

Referring now to FIGS. 1C and 1D, the fiducial marker 100*c*, 100*d* may have a positional indicator 120*c*, 120*d* that may be located at any point that provides an asymmetry to the fiducial marker 100*c*, 100*d*, and that allows for correlating a point of interest on a MRI or CT image to a point on a patient sample. In the embodiment illustrated in FIG. 1C, the positional indicator 120*c* is located along one side of the fiducial marker 100*c*, whereas in the embodiment illustrated in FIG. 1D, the positional indicator 120*d* is located near a corner of fiducial marker 100*d*. In various embodiments, the positional indicator may be a physical compression, constriction, or extension, or it may be an augmentation, such as a fold, ridge, crease, or wrinkle, so long as the positional indicator causes minimal imaging artifacts and may be visualized on the desired modalities, such as MRI and CT images. In other examples, the positional indicator may take the form of another type of augmentation, such as a bead or a clip, such as a metal clip. In various embodiments, such a clip (or other augmentation) may be attached to the body of imaging device at any position that helps define marker orientation. Another example of a suitable augmentation for use as a positional indicator is a suture ligand, ligature, or other strand, which may be tied around the body of the fiducial marker to provide a slight bend that may be appreciated on imaging and help identify position/orientation of the fiducial marker. In still other embodiments, the length of the sides of the triangle of the fiducial marker may be varied (e.g., the fiducial marker may be asymmetrical) in order to function as a positional indicator.

Figure 1E:
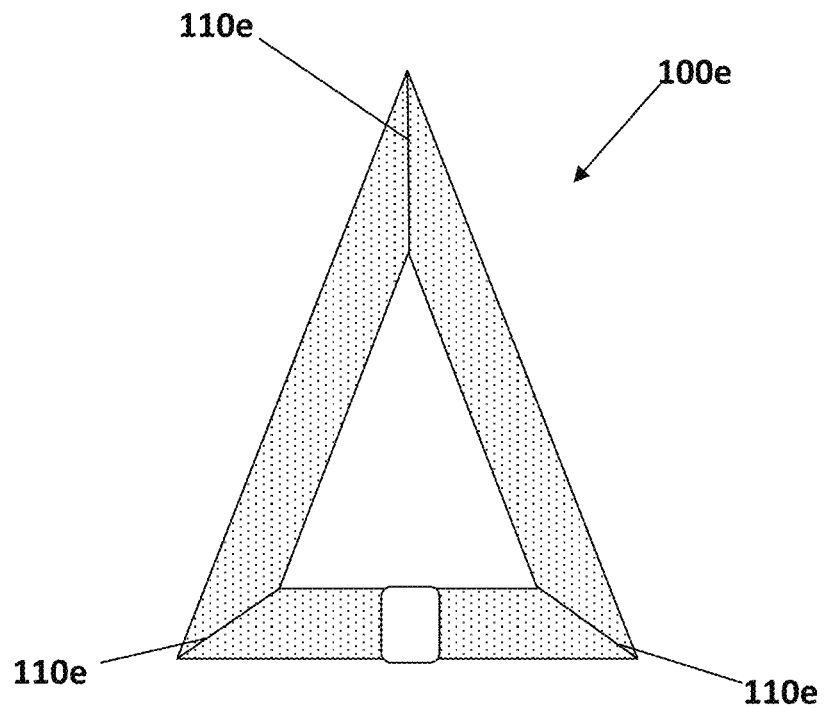

Turning now to FIG. 1E, in some embodiments, the corners 110*e* of the fiducial marker 100*de* may include a crimp, twist, fold, or any means of joining separate, adjacent casing member portions. In some embodiments, such crimps, folds, or other structure may prevent the passage of water and/or iodine from one portion of the fiducial marker to another. In other embodiments, such as those shown in FIGS. 1C and 1D, the corners may include no crimps or strictures that would impede the passage of water and/or iodine.

Figure 1F:
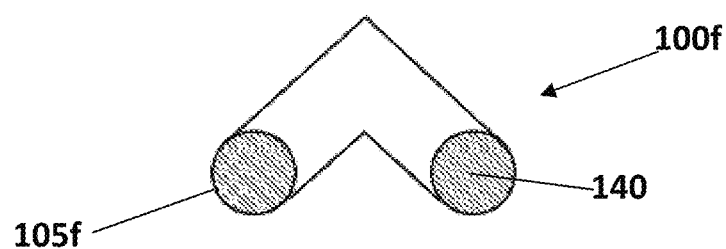

Turning now to FIG. 1F, which shows a partial cutaway view of a triangular fiducial marker 100f, in various embodiments, the sealed casing member 105f forms a hollow lumen 140 that is filled with the mixture of water and iodine. In various embodiments, the inner and outer diameters of the sealed casing member 105f and lumen 140 may be selected to optimize MRI or CT imaging. By way of example, in some embodiments, the diameter of the lumen 140 may be from 0.1 to 1.0, 0.1 to 0.9, 0.1 to 0.8, 0.1 to 0.7, 0.1 to 0.6, 0.1 to 0.5, 0.1 to 0.4, 0.1 to 0.3, or 0.1 to 0.2 cm.

Figure 1G:
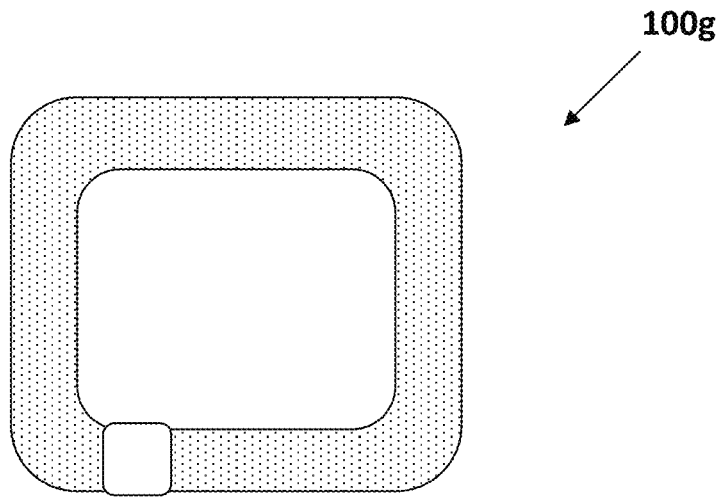
Figure 1H:
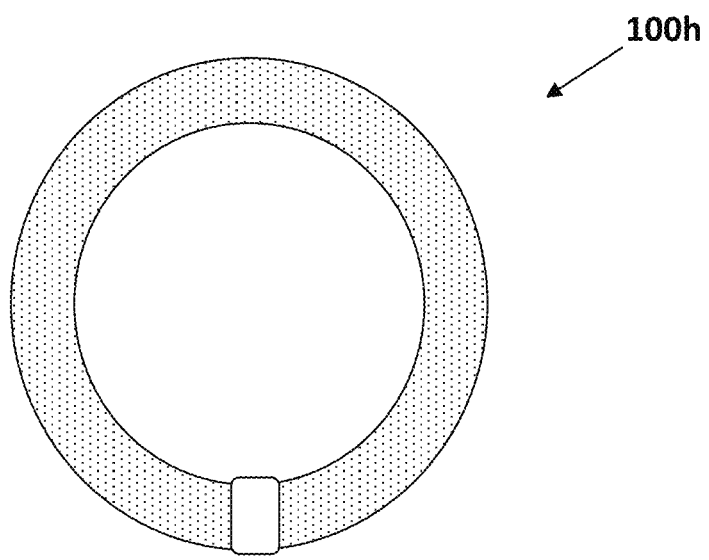
Figure 1I:
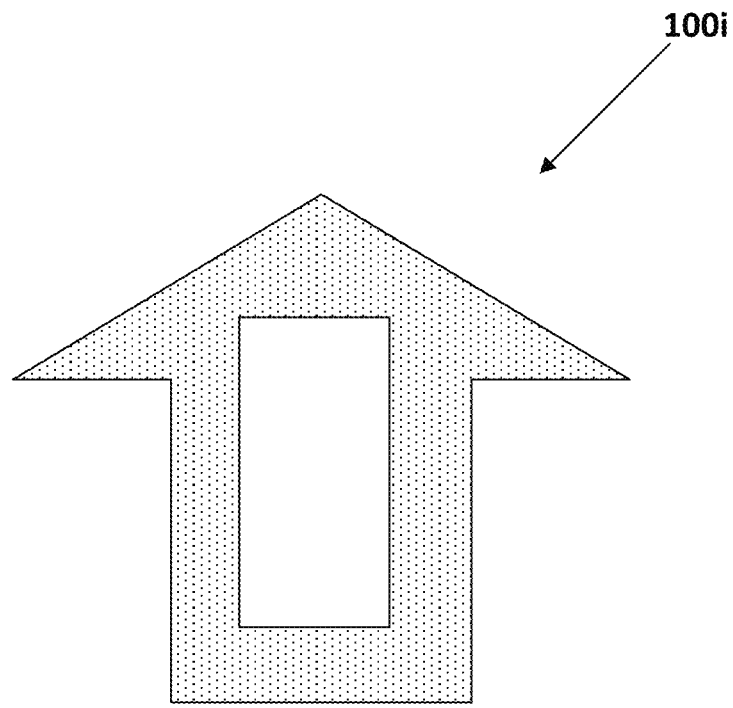
Figure 1J:
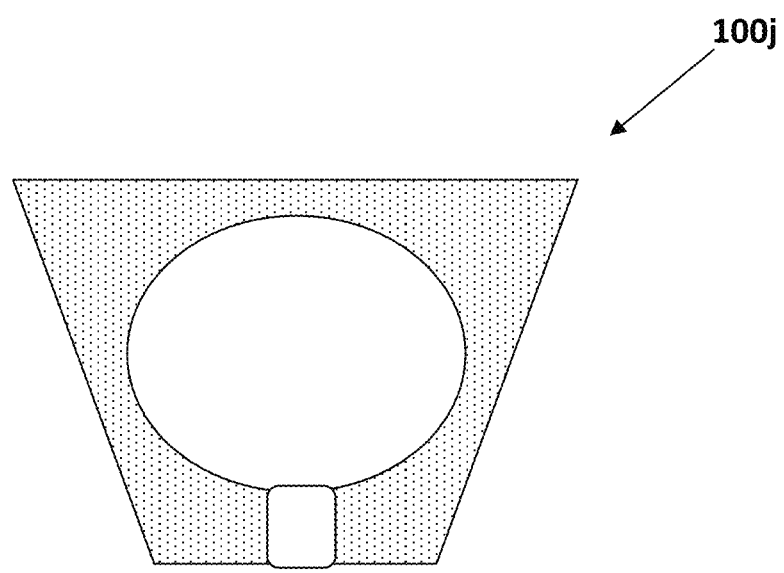

Although the examples discussed above refer to triangular fiducial markers, one of skill in the art will appreciate that the fiducial markers described herein may be formed into any desired shape, such as a rectangular fiducial marker, as shown in FIG. 1G, a circular fiducial marker, as shown in FIG. 1H, an arrow-shaped fiducial marker, as shown in FIG. 1I, and a rhomboid fiducial marker, as shown in FIG. 1J. One of skill in the art will also appreciate that fiducial markers may be formed with or without positional indicators, depending on whether the shape selected provides directionality or polarity, and depending on the particular application.

Example 2: Imaging Phantom

An imaging phantom of soft tissue attenuation was created for testing of the fiducial markers, similar to previously described protocols. Briefly, 500 ml plastic saline bottles (Baxter, Deerfield, Ill.) were emptied and filled with a gelatin mixture (Jell-O, Kraft foods, Northfield, Ill.) Two cups of boiled water was added to 24 ounces (680 g) of a powdered gelatin mixture. This was followed by an additional two cups of ice cold water. The solution was thoroughly mixed and chilled for 12 hours at 4° C. Final gelatin concentration was approximately 8%. All markers were pseudorandomly assigned a number 1 through 11 by the CT technician and labeled as such on all imaging sequences. The image evaluators were unaware of the labeling protocol used, and unblinding occurred only after data collection.

Example 3: CT Imaging and MRI Imaging

All markers were taped randomly onto the imaging phantom using two inch tape (Zonas tape, Johnson & Johnson, New Brunswick, N.J.) Helical CT scans of the phantom were performed using a 64 detector helical CT scanner (Toshiba Aquilion, Tochigi, Japan.) Helical images were acquired as a volume with 0.5 mm voxels, 0.5 sec rotation speed, 512×512 matrix, 120 kVp using a 200 mA tube current. The volume data were reconstructed in bone and soft tissue algorithms, and in isovolumetric transverse, sagittal, and dorsal planes at 2 mm slice thickness. Images were presented with window and level for soft tissue (W 120 L 40) and bone (W 2700 L 350), but observers were allowed to adjust these settings.

Following CT image acquisition, the same marker/phantom constructs were scanned with a 1.0 Tesla MRI scanner with a phased array body surface coil (GE Signa Horizon, Florence, S.C., USA.) Following scout images, T1 fat saturated transverse images and T2 weighted short tau inversion recovery (STIR) transverse, dorsal and sagittal images were obtained. The above protocols were selected because they are similar to those used clinically, and they allowed assessment of marker visibility on a T2 pulse sequences in which water is hyperintense and T1 pulse sequences, in which water is not hyperintense.

Example 4: Evaluation of Markers

To evaluate each fiducial marker, objective and subjective data were collected. A board certified radiologist and small animal surgery resident reviewed all image sequences and were blinded to the percent contrast in each marker. To measure beam hardening artifact, CT images were evaluated in a soft tissue algorithm and window and level (W 120 L 40), with instructions that the observer was allowed to change the window and level.

To quantify how well the markers were seen on CT, marker attenuation was measured in Hounsfield Units (HU) using the region of interest tool of commercially available software (eFilm, Merge HealthCare, Milwaukee, Wis.) This tool allowed marker visibility to be objectively quantified as well as assessment of the relationship between marker attenuation and its associated percent contrast. For each CT scan, attenuation of a baseline region of the phantom was measured by placing a 0.5 $cm^2$ region of interest at least 1 cm away from the marker. This served as an internal control between scans. Average attenuation with standard deviation of attenuation of each internal control region was measured in HU. Marker contrast was then reported as a ratio of marker attenuation to internal control attenuation for each scan respectively. Using this method, higher ratios indicate a greater difference between marker and phantom attenuation.

Figure 2:
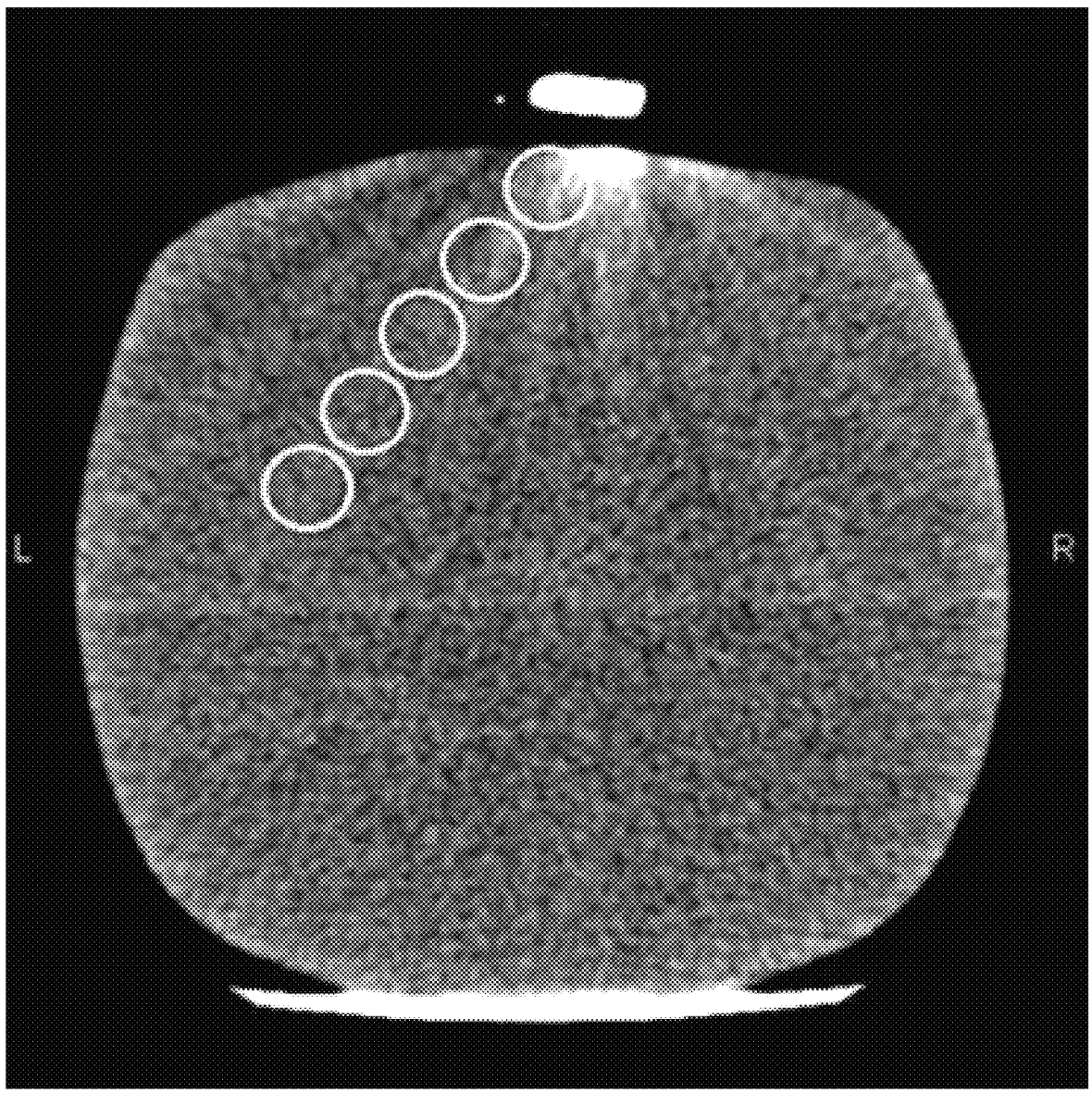
FIG. 2 illustrates a representation of the measurements made for artifact quantitation, in accordance with various embodiments

FIG. 2 illustrates a representation of the measurements made for artifact quantitation, in accordance with various embodiments. To quantify beam hardening artifact on CT images, the transverse image within each scan that had the most noticeable artifact as seen in the soft tissue algorithm was chosen for each marker and was used for all measurements of beam hardening. After this slice of "maximum artifact" had been selected, 0.5 $cm^2$ regions of interest were drawn sequentially in the phantom starting below the marker, following the longest streak line. The region closest to the marker was labeled "1", with subsequent regions labeled accordingly (regions 2, 3, 4, and 5). Average attenuation in Hounsfield units (HU) and standard deviation of each region of interest was recorded. A higher standard deviation of the selected regions would indicate more heterogeneity in the attenuation of the phantom. Beam hardening artifact was also demonstrated using these attenuation measurements and reported as a ratio to the internal control for each scan. Using this method, higher ratios indicate a greater difference between marker and phantom attenuation. The longest artifact streak length was measured using the linear measurement tool of the software, and plotted against its corresponding percent contrast.

For subjective scoring of CT artifacts, all marker sequences were given a score 1 through 3 by a board certified veterinary radiologist. Artifact was defined as any discernible streaking or image distortion. A score of 1 was given to a marker that had minimal to no artifact produced and would not be expected to alter image interpretation. A score of 2 was given to markers that produced moderate artifact which could affect image interpretation. A score of 3 was given to markers which produced severe artifact and would likely affect image interpretation.

Due to lack of a validated qualification of MRI image intensity, a subjective scoring system was used to evaluate how well the markers were seen on MRI. A score of 1 corresponded to a marker that was easily distinguished from the phantom and would likely be clinically useful. A score of 2 corresponded to a marker that could be differentiated from the phantom on most images, but was difficult to separate from the phantom in at least one or more images. A score of 3 corresponded to a marker that was quite difficult to distinguish from the underlying phantom and would be considered unreliable to use in a clinical setting.

Example 5: Statistical Analysis

All statistical analyses were performed using an open-source language and environment for statistical computing (R Core Team, 2013; freely available at http://cran.r-project.org.) Simple linear regression was used to evaluate the relationship between marker percent contrast and individual fitted factors including; marker attenuation, marker to control attenuation ratio, streak length and subjective scores for both CT and MRI. For relationships analyzed, coefficient of determination (r-squared) values are reported along with associated p-values. Where applicable, slope of the regression line is reported (slope +/− standard error, p-value). A p<0.05 was considered significant. Assumptions of simple linear regression including linearity, constant variance and normal distribution of the subpopulations were verified.

Example 6: Results

In total, 11 markers containing percentages of iopamidol 300 of 0%, 10%, 20%, 30%, 40%, 50%, 60%, 70%, 80%, 90% and 100% were imaged. Mean CT control attenuation ranged from 83.7 to 84.9 HU with no relationship found between the control region attenuation and marker percent contrast medium (R-square=−0.0072, p=0.8).

Figure 3:
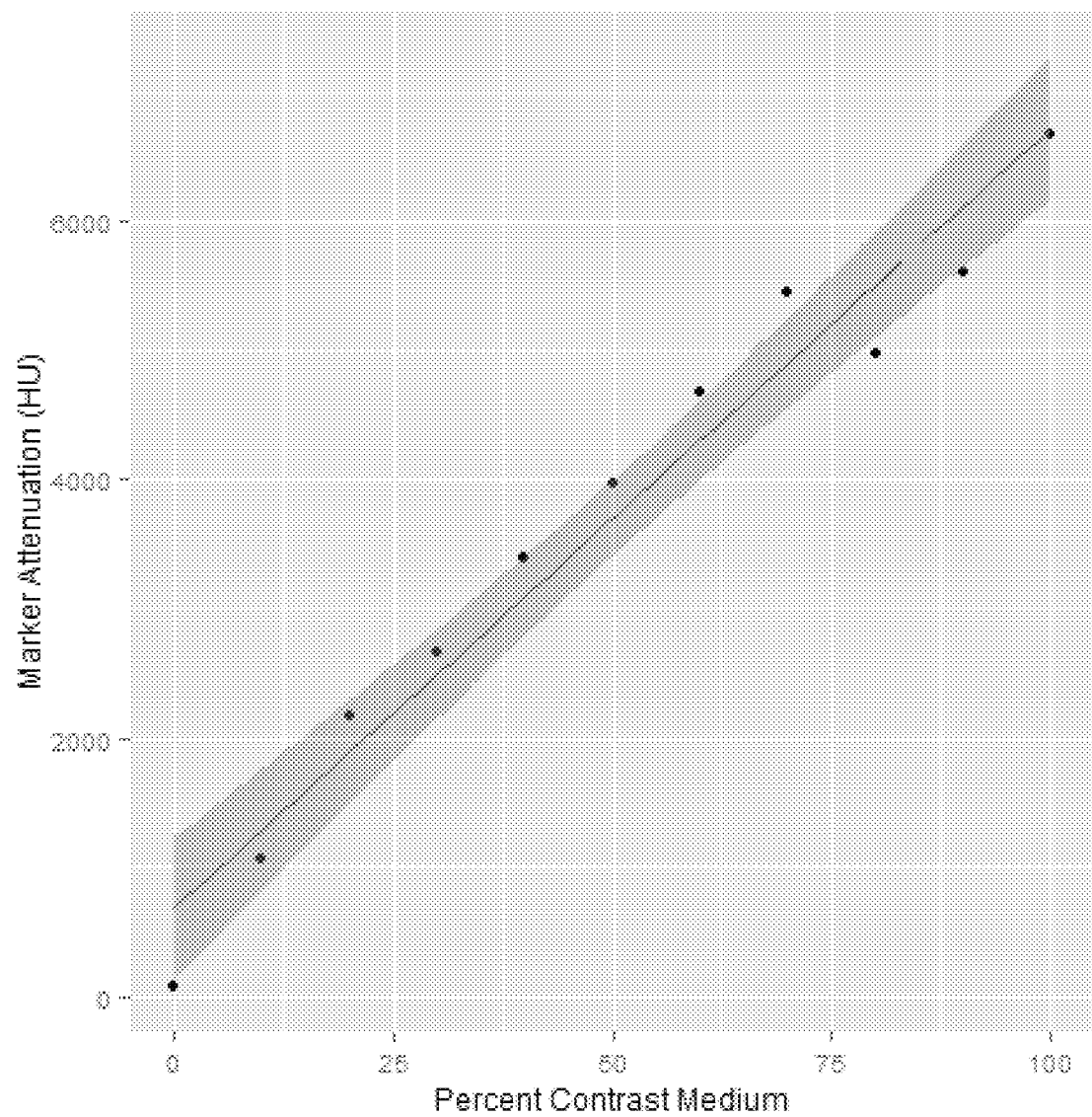
FIG. 3 illustrates a linear regression analysis of attenuation of each marker against percent contrast, in accordance with various embodiments.

FIG. 3 illustrates a linear regression analysis of attenuation of each marker against percent contrast, in accordance with various embodiments. A strong positive linear correlation between these two variables was noted (adjusted $R^2$=0.96, p<0.001.) The percent contrast medium in each marker was correlated to its corresponding CT attenuation measurements. Linear regression analysis revealed that for every 10% increase in marker contrast medium percentage, average marker attenuation increased by 60.3 HU (+/−4.12 HU, p<0.0001). Ratios of the attenuation of each marker compared to that of the internal control for their respected scans were calculated (Table 1). The marker with 0% iopamidol showed no difference in attenuation (ratio=0.86).

TABLE 1

| Percent Contrast Medium | CT score | MRI score* | Marker Attenuation (HU) | Control Attenuation (HU) | Marker:control ratio | Streak Length (cm) |
|---|---|---|---|---|---|---|
| 0 | 1 | 1 | 72.5 | 84.4 | 0.859 | 1.2 |
| 10 | 1 | 2 | 1065.5 | 83.9 | 12.7 | 1.0 |
| 20 | 2 | 1 | 2170.4 | 83.8 | 25.9 | 2.4 |
| 30 | 2 | 2 | 2659.6 | 83.9 | 31.7 | 3.3 |
| 40 | 2 | 2 | 3402.0 | 84.0 | 40.5 | 4.3 |
| 50 | 2 | 2 | 3975.8 | 83.7 | 47.5 | 4.0 |
| 60 | 3 | 3 | 4676.0 | 83.8 | 55.8 | 4.6 |
| 70 | 2 | 2 | 5454.2 | 84.3 | 64.7 | 3.8 |
| 80 | 2 | 2 | 4978.7 | 84.1 | 59.5 | 3.6 |
| 90 | 3 | 3 | 5602.8 | 84.0 | 66.7 | 5.8 |
| 100 | 3 | 3 | 6670.1 | 83.9 | 79.5 | 5.2 |

Subjective computed tomography score, magnetic resonance imaging score, marker attenuation, control attenuation, marker: control attenuation ratio and streak length for each marker contrast percentage. A positive correlation between marker contrast and CT subjective score, MRI subjective score, marker attenuation and streak length was seen. The ratio of marker: control attenuation is also reported. For the subjectivity scores, for CT 1 is no artifact, 2 = some artifact that could interfere with image interpretation and 3 is artifact that would interfere with image interpretation, for MRI 1 = easily detected, 2 = detectable and 3 is difficult to detect. Ratios at or near 1 indicate minimal difference between the marker and phantom, making them difficult to distinguish. Higher ratios indicate a greater difference in marker to phantom contrast and are easily seen on CT.
*Column indicates MRI short-tau inversion recovery scores (T2 weighted)

Figure 4:
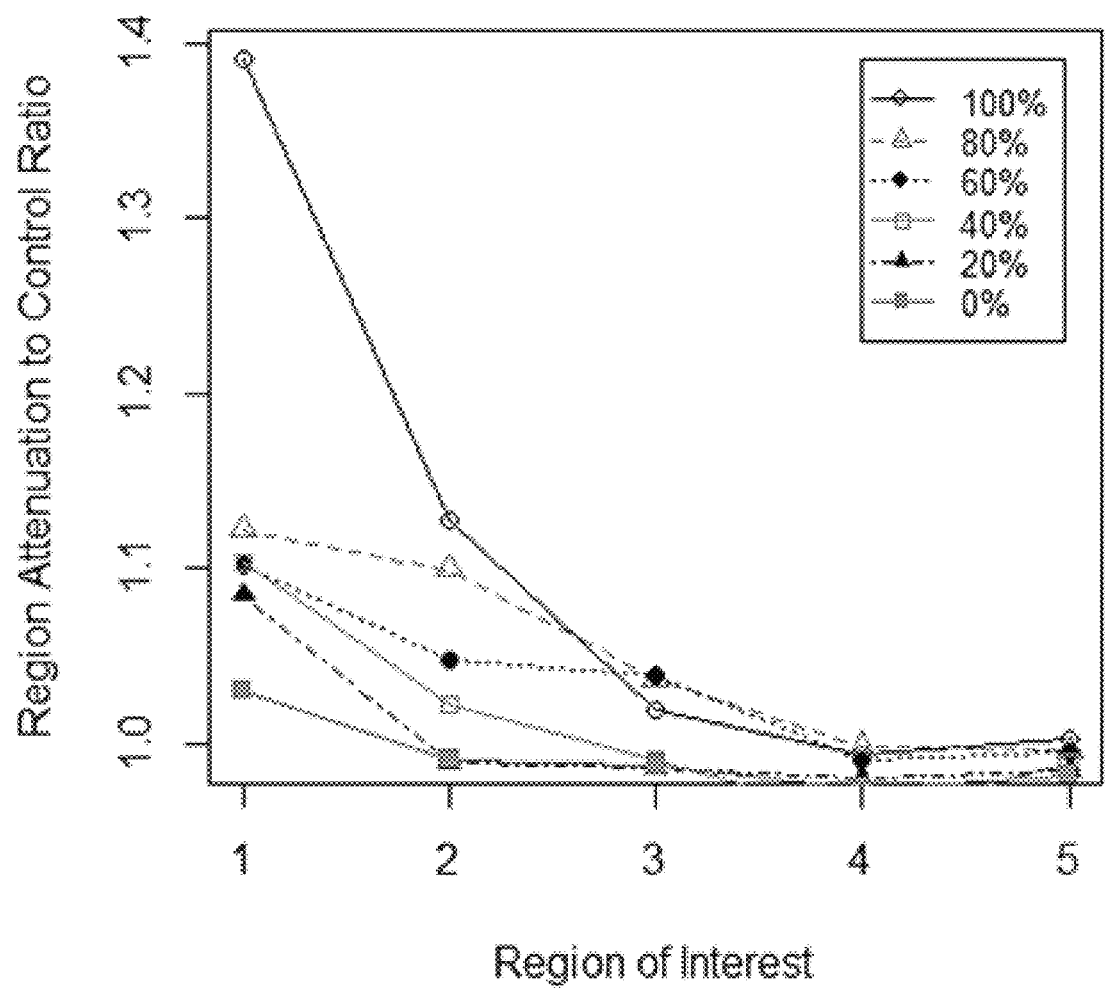
FIG. 4 is a graph illustrating the mean attenuation of regions 1 through 5 reported as a ratio to the control attenuation for selected markers, in accordance with various embodiments.
Figure 5:
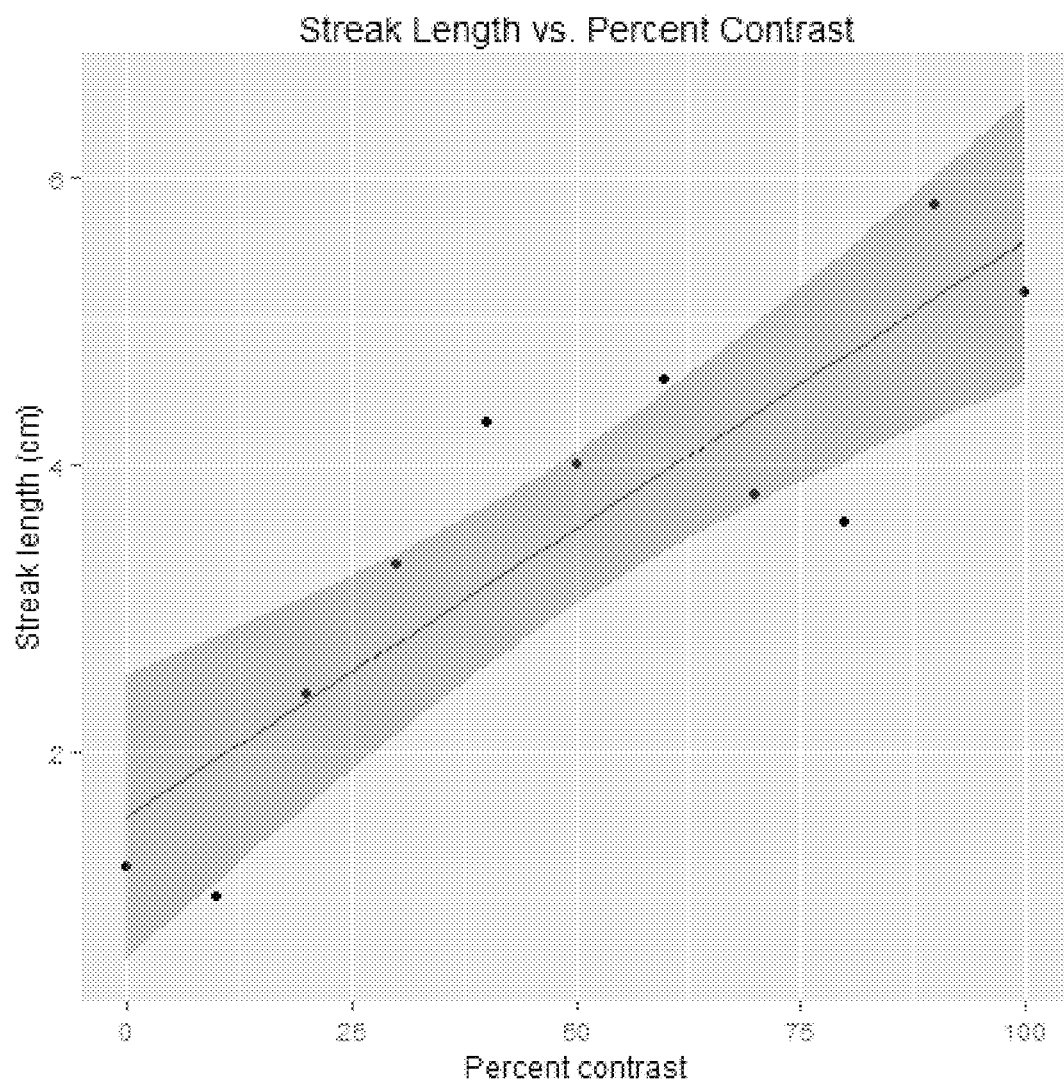
FIG. 5 is a graph illustrating a simple linear regression line showing the relationship between percent contrast and streak length on CT images, in accordance with various embodiments.

FIG. 4 is a graph illustrating the mean attenuation of regions 1 through 5 reported as a ratio to the control attenuation for selected markers. Areas closest to the marker and areas from the highest percent contrast medium markers showed the most significant difference in attenuation from the control. A positive correlation between marker contrast medium and standard deviation in region 1 was found ($r^2$=0.826, p=0.0001). It was noted that all markers tested, including the marker with 0% contrast medium, showed some degree of x-ray attenuation in region 1. No difference in the attenuation of area 2 was seen for markers of 0, 10 and 20%. FIG. 5 is a graph illustrating a simple linear regression line showing the relationship between percent contrast and streak length on CT images, in accordance with various embodiments. A positive correlation between longest measured streak and marker contrast medium concentration was found ($r^2$=0.765, p=0.0004).

FIGS. 6A-6D illustrate four representative computed tomography (FIGS. 6A and 6B) and magnetic resonance imaging (FIGS. 6C and 6D) of markers containing 10% (FIGS. 6A and 6C) and 70% (FIGS. 6B and 6D) contrast medium, in accordance with various embodiments. The 10% marker was easily viewed on CT and received a CT subjective score of 1 (FIG. 6A), indicating no significant artifact production. The 70% marker received a CT subjective score of 2, indicating moderate artifact production. Both the 10% and 70% marker received a subjective MRI score of 2 (viewed in most images). Markers made with higher percentage of iodinated contrast trended towards higher CT subjective scores (Table 1, FIGS. 6A-6B). A correlation between CT subjective score and marker percent contrast medium was found ($r^2$=0.669, p=0.002). Subjective scores indicated that the lowest concentration of iopamidol tested (10%, mean attenuation 1065.5 HU) was clearly and distinctly seen on CT images.

No significant artifacts were noted on MRI images. MRI subjective scores indicated that markers with a percentage of iopamidol greater than 50% resulted in a less readily identifiable marker on STIR MRI pulse sequences (Table 1, FIGS. 6C-6D). There was a positive correlation between percent contrast medium in each marker and MRI STIR subjective score ($r^2$=0.6, p=0.005). While the markers were visible on MRI T1 sequences, no correlation between marker percent contrast and subjective score was seen.

Example 7: Discussion

Disclosed herein are fiducial markers that are easily detected on both CT and MRI, and that minimize beam hardening artifact on CT. To assess degree of contrast between the markers and normal soft tissues on CT, attenuation of markers was measured in HU that were made with an in increasing percentage of an iopamidol solution mixed with water. Marker attenuation was then compared to phantom attenuation and reported as a ratio. With the addition of 10% of the iodinated contrast medium solution, marker attenuation was over ten times that of the soft tissue phantom. This relationship continued in a linear fashion for each incremental increase in iodinated contrast solution. Normal soft tissues have a mean attenuation of 40-60 HU. Thus, this increase in attenuation of the 10% marker to 1065 HU made it readily detectable on CT images with a contrast ratio of 12.7. While markers with a higher percentage of iopamidol contrast medium yielded a higher marker to phantom ratio, they also produced a greater intensity of CT beam hardening artifact, making these higher percentage markers less suitable as a fiducial marker for CT imaging.

To quantify beam hardening artifact on CT, streak length of any perceived artifact was measured for each marker. Furthermore, sequential regions of interest were drawn below each marker and attenuation of these regions was compared to that of the phantom control. Percent contrast medium was also found to be strongly correlated to degree of beam hardening artifact as determined by length of streaking and change in attenuation of regions below the marker. CT subjective scores assigned by a board certified veterinary radiologist mirrored objective measurements of artifact production. The ideal marker would display the least amount of CT artifact. Based on the above testing methods, the 10% marker best fit our definition of an ideal fiducial marker for CT imaging because it generated the least amount of CT artifact (specifically, no changes in attenuation in area 2 and low measured streak artifact), and was readily detectable on CT images with a factor of 12.7 difference in attenuation between the 10% marker and the phantom.

On MRI, water is hyperintense on multiple pulse sequences including T2 and STIR pulse sequences, while water is hypointense on T1 and FLAIR pulse sequences. In vivo, diseased tissues typically have increased water content compared to surrounding normal tissues, which makes the diseased tissues hyperintense and conspicuous on T2 and T2 weighted STIR pulse sequences. MRI intravenous gadolinium contrast medium can also make these tissues hyperintense on T1 post-contrast pulse sequences. Both T2 weighted STIR and T1 fat saturation spin echo pulse sequences were used herein to assess the fiducial markers. The ability to see the markers on MRI was subjectively scored by a blinded radiologist. As expected, a higher water content in the markers (lower percent contrast medium) resulted in greater hyperintensity on T2 weighted STIR pulse sequences, which was reflected in our scoring system. Interestingly, the markers were also visible on the T1 fat saturation images, possibly secondary to the plastic in the IV tubing. In general, the visibility scores were less on the T1 compared to STIR images, and there was no correlation between marker percent contrast and visibility on T1 weighted images. Based on these data, the markers with a percentage of iopamidol contrast medium of 50% or lower were the best fiducial markers for MRI imaging. Thus, combining the findings of the MRI and CT imaging, we conclude that the overall best fiducial marker for both imaging modalities was the 10% iopamidol 300 contrast medium solution.

Thus, disclosed herein are easily made and effective fiducial markers compatible with both CT and MRI. Previous studies have described the use of metal as a fiducial marker for computed tomography. While CT metal artifacts can be reduced by reducing the size of the marker and using metal artifact reducing (MAR) algorithms, the properties of may solid metals make them inappropriate choices for MRI. The MRI susceptibility artifact is well described when ferrous metals cause disturbances in the local magnetic field, thereby shifting the position of the image. This artifact causes large regions of severe distortion of the image, rendering part or all of the image as non-diagnostic. This artifact makes a metallic fiducial marker unsuitable for use with both CT and MRI. Vitamin E capsules taped to the skin have been used as fiducial markers for MRI. Unfortunately, these protocols have proven to be inaccurate for surgical planning, due to the shape of the capsules. Unlike prior art fiducial markers, the fiducial markers disclosed herein are easily adhered to the skin, and may be sutured to the skin if needed when formed in a triangular shape. Furthermore, vitamin E is isoattenuating to soft tissue on CT, and would not have adequate contrast on CT for use as a fiducial marker for soft tissue imaging.

The linear attenuation coefficient commonly described in X-ray physics refers to the degree of x-ray photon attenuation per unit of path length. This coefficient increases with increased electron density of a tissue. Compounds having atoms of high atomic number (Z) are considered more opaque on x-rays or more attenuating on CT due to this phenomenon. Notable contrast medium compounds frequently used in medicine include barium and iodine. As described previously, iopamidol is an iodinated, non-ionic compound and its use in both human and veterinary medicine is highly documented. However, as disclosed herein, the use of 100% iopamidol 300 solution did not result in adequate marker intensity on MRI and provided excessive artifact on CT. To address this issue, water was used to dilute the iodinated solution, until the most suitable concentration was identified.

Thus, disclosed herein are fiducial markers that may be easily created from IV infusion tubing, filled with 10% iopamidol 300 iodinated contrast medium, and sealed into the shape of a triangle. The preferred concentration of iodinated contrast was found to be relatively low concentration (10%, or about 30 mg/ml iodine) as this provided sufficient attenuation for visualization on both CT and MRI without excessive beam hardening artifact on CT.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:
1. A fiducial marker comprising:
a single sealed casing member that forms a closed shape with an opening to indicate a region of interest, the single sealed casing member filled with a solution consisting of a nonionic iodinated contrast agent and water at a concentration of 30-60 mg/ml iodine; wherein the solution is distinguishable on both MRI and CT, and wherein the single sealed casing member is the only sealed casing member of the fiducial marker; and
a positional indicator that is offset from a center of the opening of the single sealed casing member and dis- tinguishable on both the MRI and CT imaging modalities to identify an orientation of the fiducial marker in both the MRI and CT imaging modalities, wherein the positional indicator is a crimp, physical compression, constriction, extension, augmentation, fold, ridge, crease, or wrinkle in the sealed casing member, or is coupled to the sealed casing member.

2. The fiducial marker of claim 1, wherein the solution consisting of the nonionic iodinated contrast agent and water comprises 30 mg/ml iodine.

3. The fiducial marker of claim 1, wherein the single sealed casing member comprises a plastic or elastomeric material.

4. The fiducial marker of claim 3, wherein the plastic or elastomeric material includes polyvinyl chloride (PVC) polypropylene, latex, nylon, or dynaflex.

5. The fiducial marker of claim 3, wherein the plastic or elastomeric material comprises a length of IV tubing sealed at each of two ends.

6. The fiducial marker of claim 5, wherein the IV tubing is crimped to form the closed shape.

7. The fiducial marker of claim 6, wherein the closed shape is a triangle.

8. A method of making a fiducial marker, comprising:
   filling a single casing member with a solution consisting of a nonionic iodinated contrast agent and water at a concentration of 30-60 mg/ml iodine;
   sealing the single casing member, wherein the single sealed casing member is the only sealed casing member of the fiducial marker;
   forming the single sealed casing member into a closed shape with an opening to indicate a region of interest; and
   providing the fiducial marker with a positional indicator configured to identify the orientation of the fiducial marker in both MRI and CT imaging modalities, wherein the positional indicator is a crimp, physical compression, constriction, extension, augmentation, fold, ridge, crease, or wrinkle in the sealed casing member, or is coupled to the sealed casing member.

9. The method of claim 8, wherein filling the single casing member with the solution consisting of the iodinated contrast agent and water comprises filling the single casing member with the solution comprising a concentration of 30 mg/ml iodine.

10. The method of claim 8, wherein the nonionic iodinated contrast agent is iopromide or iohexol.

11. The method of claim 8, wherein the nonionic iodinated contrast agent is iopamidol.

12. The method of claim 8, wherein the single casing member comprises a plastic or elastomeric material.

13. The method of claim 12, wherein the plastic or elastomeric material includes polyvinyl chloride (PVC) polypropylene, latex, nylon, or dynaflex.

14. The method of claim 12, wherein the plastic or elastomeric material comprises a length of IV tubing sealed at each of two ends.

15. The fiducial marker of claim 1, wherein the nonionic iodinated contrast agent is iopamidol.

16. The fiducial marker of claim 1, wherein the nonionic iodinated contrast agent is iopromide or iohexol.

* * * * *